US008638431B2

(12) United States Patent
Ashok et al.

(10) Patent No.: US 8,638,431 B2
(45) Date of Patent: Jan. 28, 2014

(54) FIBER PROBE BASED MICROFLUDIC RAMAN SPECTROSCOPY (75) Inventors: Praveen Cheriyan Ashok, St Andrews (GB); Gajendra Pratap Singh, St Andrews (GB); Kishan Dholakia, St Andrews (GB); Khay Tan, St Andrews (GB)

(73) Assignee: University Court of the University of St Andrews, St Andrews (GB)

( * ) Notice: Subject to any disclaimer, the term of this patent is extended or adjusted under 35 U.S.C. 154(b) by 345 days.

(21) Appl. No.: 12/892,640

(22) Filed: Sep. 28, 2010

(65) Prior Publication Data

US 2012/0075627 A1    Mar. 29, 2012

(51) Int. Cl.
*G01J 3/44*    (2006.01)

(52) U.S. Cl.
USPC ........................................................ 356/301

(58) Field of Classification Search
USPC ........................................ 356/301, 244–246
See application file for complete search history.

(56) References Cited

U.S. PATENT DOCUMENTS

| 5,302,272 | A | * | 4/1994 | Klein | 356/344 |
| 5,736,410 | A | * | 4/1998 | Zarling et al. | 356/417 |
| 5,862,273 | A | * | 1/1999 | Pelletier | 356/318 |
| 6,020,207 | A | * | 2/2000 | Liu | 436/164 |
| 6,166,804 | A | * | 12/2000 | Potyrailo et al. | 356/318 |
| 6,571,118 | B1 | * | 5/2003 | Utzinger et al. | 356/318 |
| 6,825,928 | B2 | * | 11/2004 | Liu et al. | 356/317 |
| 6,870,165 | B2 | * | 3/2005 | Amirkhanian et al. | 250/458.1 |
| 6,907,149 | B2 | * | 6/2005 | Slater | 356/318 |
| 2007/0048746 | A1 | * | 3/2007 | Su et al. | 435/287.2 |
| 2007/0262265 | A1 | * | 11/2007 | MacCraith et al. | 250/461.2 |

OTHER PUBLICATIONS

P. C. Ashok et al., "Fiber probe based microfluidic raman spectroscopy"; Optics Express, vol. 18, No. 8, Apr. 12, 2010; pp. 7642-7649.

* cited by examiner

*Primary Examiner* — Kara E Geisel
(74) *Attorney, Agent, or Firm* — W. Kevin Ransom; Moore & Van Allen PLLC (57) ABSTRACT A microfluidic device comprising at least one microfluidic channel with an input and an output for allowing fluid flow; and at least one Raman fiber based probe having an excitation fiber probe and/or a collection fiber probe positioned so that one end of the probe is in the microfluidic channel.

11 Claims, 8 Drawing Sheets

FIBER PROBE BASED MICROFLUDIC RAMAN SPECTROSCOPY

FIELD OF THE INVENTION

The present invention relates to a fiber probe based system for performing Raman spectroscopy in a microfluidic platform.

BACKGROUND OF THE INVENTION

Raman spectroscopy is a powerful and effective tool for analytical studies of biological and chemical samples. Raman scattering is inelastic light scattering from a sample that may yield a molecular fingerprint of the constituent molecules. An inherent limitation of this technique is the low Raman cross section of bio-molecules. Hence, long integration times are required to obtain good signal to noise ratio. Nevertheless, Raman spectra have rich information content and a single Raman spectrum can provide information about all the molecular constituents of the sample.

Raman spectroscopy has been combined with microfluidic system. To overcome the limitation of the inherently low Raman cross section, Surface Enhanced Raman Spectroscopy (SERS) based detection schemes have been employed in microfluidic systems. Other experiments have used confocal Raman microscopy for online monitoring of chemical reactions. In all these applications, monitoring was performed through a combination of a bulk Raman microscope and a microfluidic chip. A problem of using microscope based systems to collect Raman data from such microfluidic chips is that the signal is acquired through a substrate which has its own background signal. This limits the detection efficiency of the system. Using a microscope also precludes miniaturization.

Figure 1:
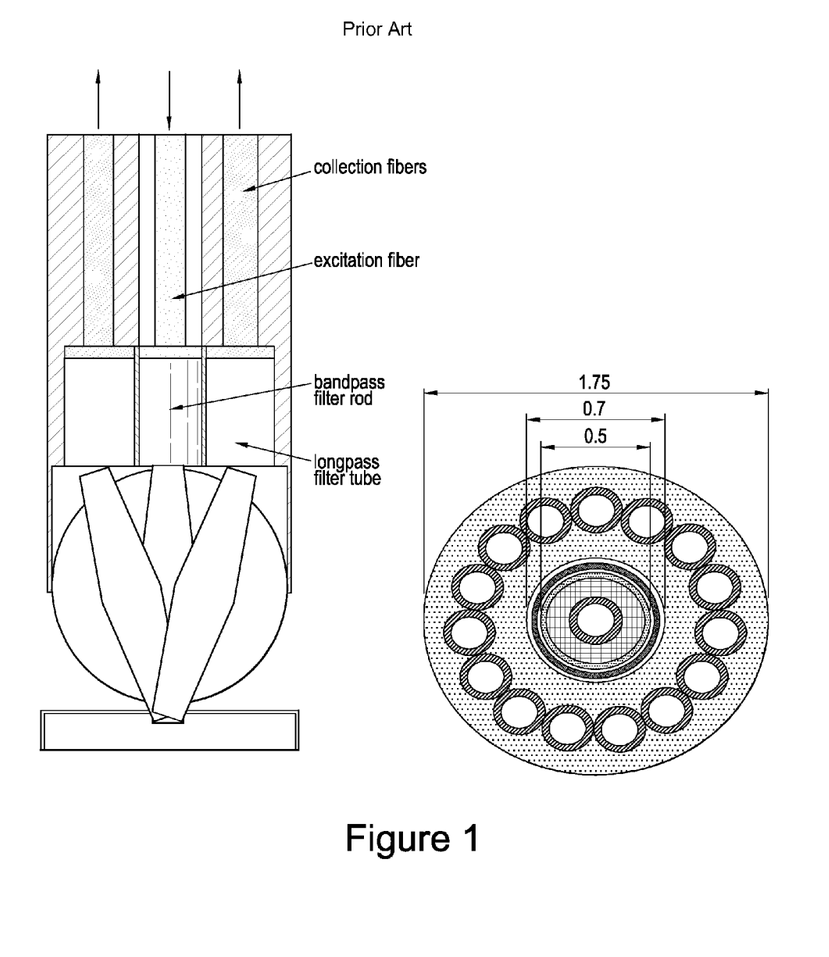
FIG. 1 shows an example of a known Raman fiber probe.

FIG. 1 shows an example of a known Raman fiber probe. This has a central excitation fiber and several collection fibers arranged around it. All fibers carry an appropriate filter at their tips for Raman spectroscopy applications: a bandpass filter for the excitation fiber, and a longpass filter for the collection fibers. In this arrangement, the head of the probe is shared by both the excitation and the collection fibers, with both fibers facing in the same direction. An advantage of this design is its overall small shape. A disadvantage is that it is relatively complex and expensive to make. In addition, the Raman excitation and collection fibers are bundled together and lack flexibility to inspect samples at different angles between the collection probe and the excitation probe. A further disadvantage is that the configuration is not optimized for the filters. The filter works at its maximum efficiency when the beam is perpendicular to the entrance surface of the filter. Hence, in this design, where a non-collimated beam passes through the filters, filter efficiency is reduced.

Figure 2:
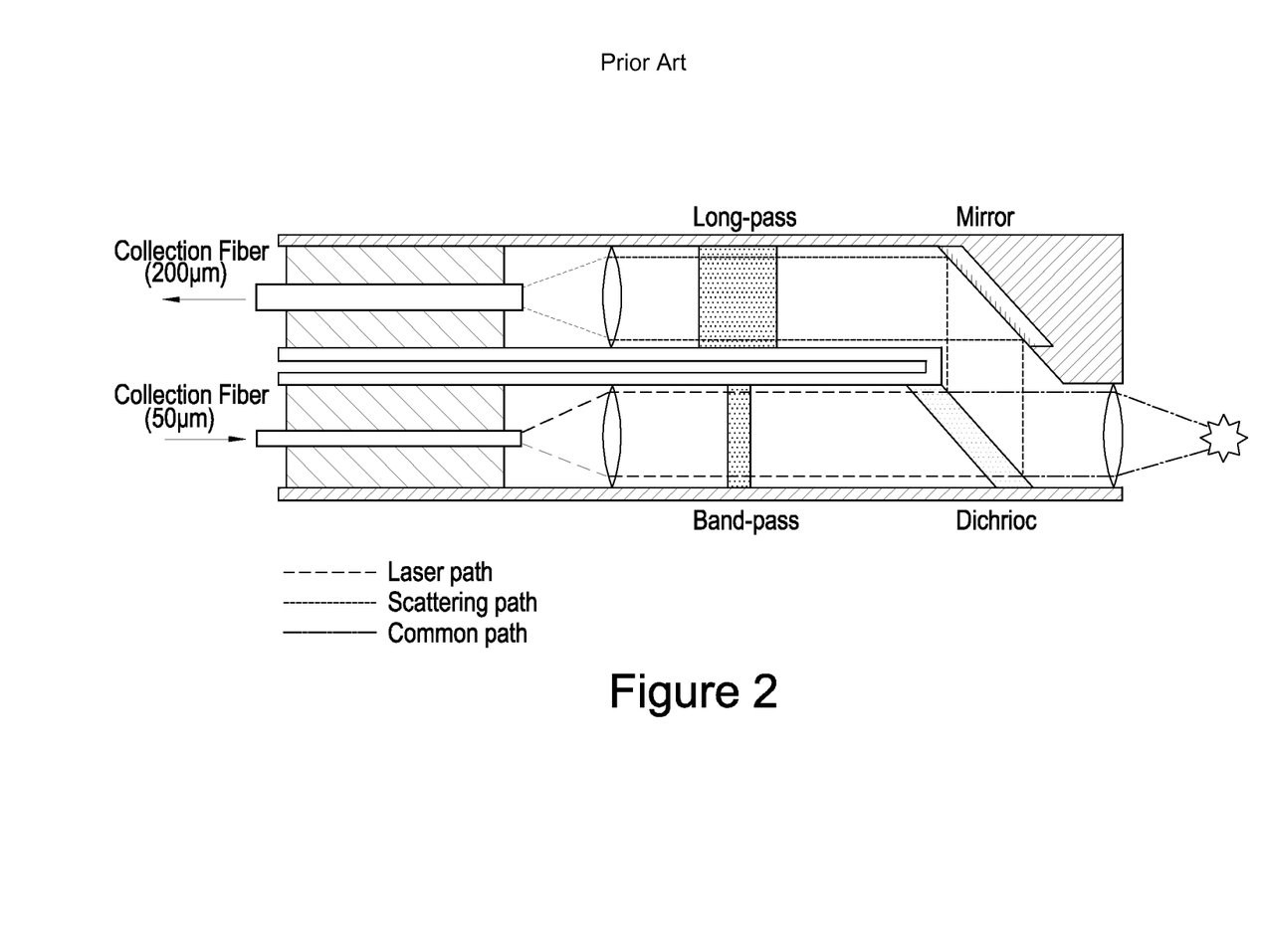
FIG. 2 shows an example of another Raman fiber probe.

FIG. 2 shows an example of another probe. In this case, there is a single excitation fiber and a single collection fiber arranged in separate parallel tubes. At the output of the excitation fiber is a bandpass filter, a dichroic mirror, and lens, which focuses the excitation light onto a sample area. Light incident on the sample causes Raman excitation and consequently the emission of a Raman signal. The Raman signal passes through a long pass filter for collection in the collection fiber. As with the arrangement of FIG. 1, in the device of FIG. 2, the head of the probe is shared by both the excitation and the collection fibers, with both fibers facing in the same direction. An advantage of this design is its overall small shape. However, whilst this arrangement is more appropriate for the filters because of the collimated beam, it is difficult to manufacture and provides limited flexibility in terms of angles of excitation and collection.

SUMMARY OF THE INVENTION

According to the present invention there is provided a microfluidic device comprising at least one microfluidic channel with an input and an output for allowing fluid flow; at least one fiber based Raman probe is provided. The fiber based Raman probe may include one or more excitation probes and/or one or more collection probes. The at least one excitation probe is positioned so that its output is in the microfluidic channel. The at least one collection probe is positioned so that its input is in the at least one microfluidic channel.

Here, "probe" includes the fiber and one or more associated optical components, for example a collimating lens, one or more filters and a focusing lens.

Preferably, the excitation probe and the collection probe are orthogonal to each other. The excitation probe and/or the collection probe may be orthogonal to the microfluidic channel.

Preferably, the excitation probe and the collection probe are positioned to point in different directions. For example, the excitation probe and the collection probe may be collinearly arranged but positioned opposite each other.

Since the excitation and collection probes are directly inserted into a microfluidic channel, collected Raman spectra are free from any background signal coming from the substrate of the microfluidic chip. Also, the system is free from alignment issues as the fiber insertion channels are pre-determined relative positions defined during the fabrication of the microfluidic chip. Furthermore, the device can be miniaturized whilst being simple to manufacture.

The excitation fiber probe may contain a bandpass filter, so that only the excitation light passed through the probe to the sample area. The bandpass filter may allow only light with wavelength 785 nm to pass. The bandpass filter may be placed between a pair of achromatic doublets.

The collection fiber probe may contain a longpass filter. The long pass filter is selected to block the excitation light, so that only sample emissions are collected. The long pass filter may block 785 nm light. The longpass filter may be placed between a pair of achromatic doublets.

BRIEF DESCRIPTION OF THE DRAWINGS

Various aspects of the invention will now be described by way of example only and with reference to the accompanying drawings, of which:

FIGS. 3(a) and (b) show perspective views of an integrated microfluidic fiber based Raman device in which the excitation and collection paths are orthogonal;

FIG. 3(c) is a plan view of an integrated microfluidic fiber based Raman device in which the excitation and collection paths are collinear;

DETAILED DESCRIPTION OF THE DRAWINGS

FIGS. 3(a) and 3(b) show an integrated fiber based Raman microfluidic chip 10 with an orthogonal collection geometry. The chip has two sets of internal channels, fiber probe channels for locating Raman fiber collection and excitation probes 14 and 16 and a microfluidic channel 18 that has an input and output to allow fluid to flow through it. In this example, the excitation and collection channels, and consequently the excitation and collection probes 14 and 16, are mutually orthogonal. All the channels are fabricated with same dimension of the fiber probe heads, for example an outer diameter of 3 mm. The excitation probe 14 and the collection probe 16 are inserted into the chip 10 through the fiber channels and the detection analyte is flown through the fluidic channel. The physical dimension of the chip 10 with inserted probe heads 14 and 16 is relatively small, for example 25 mm×30 mm.

FIG. 3(c) shows an integrated fiber based Raman microfluidic chip 20 with a collinear excitation/collection geometry. As before, the chip 20 has two sets of internal channels, fiber probe channels for locating Raman fiber collection and excitation probes 22 and 24 and a microfluidic channel 26 that has an input and output to allow fluid to flow through it. In this example, the excitation and collection channels are collinear, and the probe heads 26 and 28 are arranged to be directly facing each other. Again, all the channels are fabricated with same dimension of the fiber probe heads 26 and 28, for example an outer diameter of 3 mm. The excitation probe and the collection probe heads 26 and 28 are inserted into the chip through the fiber channels and the detection analyte is flown through the fluidic channel 26. As for the device of FIGS. 3(a) and 3(b) the physical dimension of the chip 20 with inserted probe heads can be made relatively small, for example 25 mm×30 mm.

Figure 3:
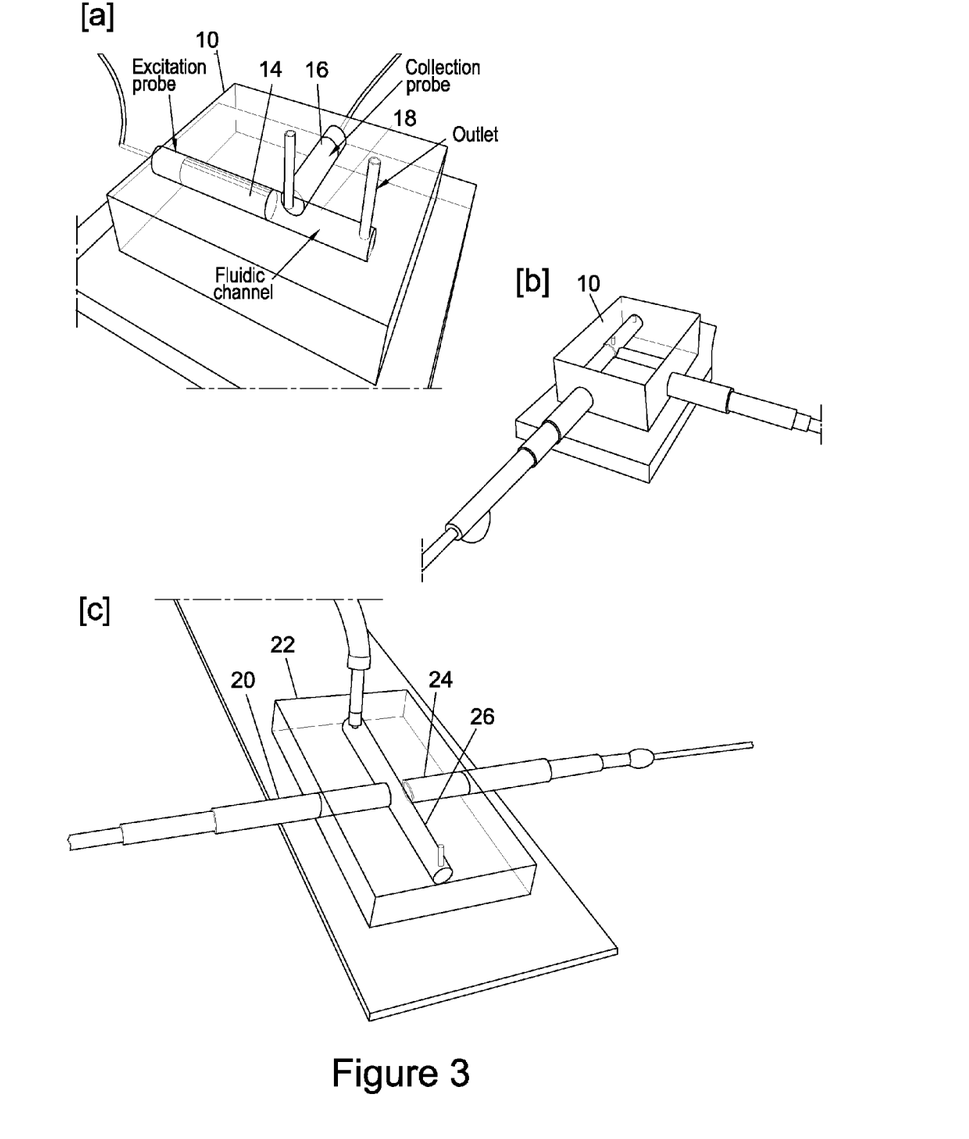
Figure 4A:
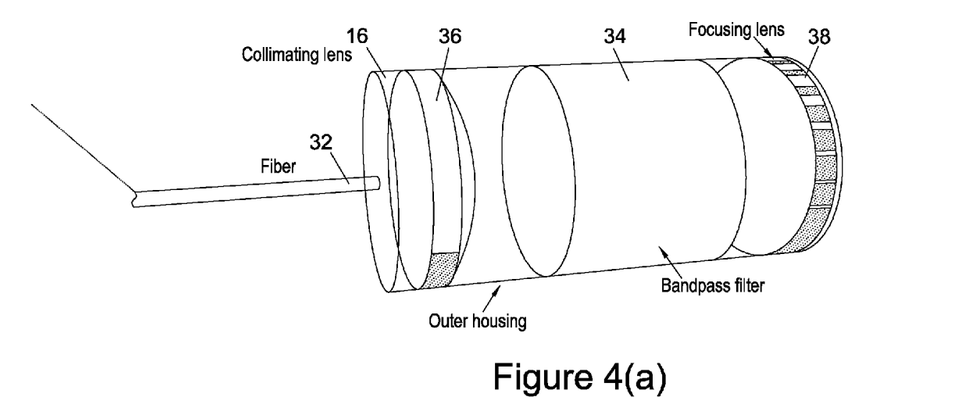
FIG. 4(a) is a cross section through an excitation probe head for use in the integrated devices of FIGS. 3(a) to (c)

FIG. 4(a) shows an excitation probe head for use in the devices of FIG. 3. This has an outer housing 30 in which are located the end of an optical fiber 32, and a bandpass filter 34 positioned between a collimator 36 (for example a pair of achromatic doublets) and a focusing lens 38. The bandpass filter 34 may be operable at any suitable wavelength matched to allow only the excitation wavelength to pass, but as an example is selected to allow only light with a 785 nm wavelength to pass through it. The collimator 36 is used for collimation of the light before the filter 34. This ensures that the filter works at its maximum efficiency. After the filter 34, the lens 38 is provided for focusing the light onto the sample area.

Figure 4B:
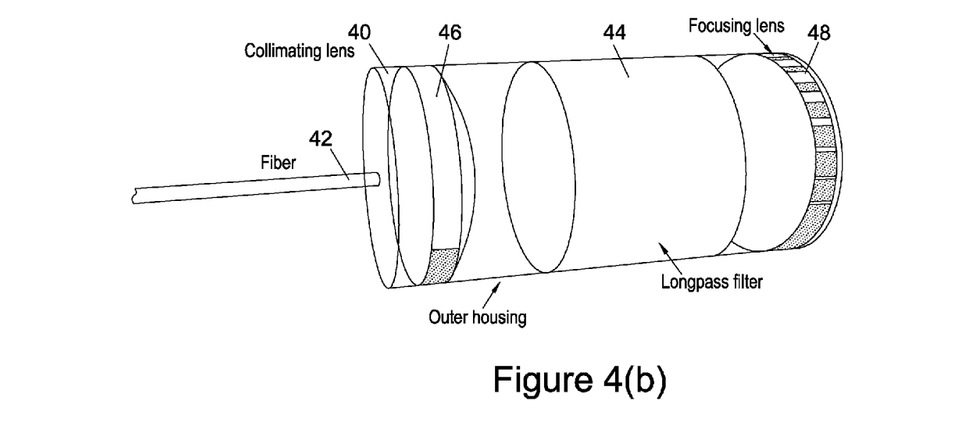
FIG. 4(b) is a cross section through a collection probe head for use in the integrated devices of FIG. 3(a) to (c)

FIG. 4(b) shows a collection probe head for use in the devices of FIG. 3. This has an outer housing 40 in which are located the end of the collection optical fiber 42, and a longpass filter 44 positioned between a collimator 46 (for example a pair of achromatic doublets) and a focusing lens 48. The longpass filter 44 is selected to block the excitation signal wavelength but allow Raman emissions to be collected. For the example given above, the longpass filter 44 is adapted to block light with a 785 nm wavelength. The collimator 46 is used for collimation of the light before the filter. After the filter 44, a lens is provided 48. This has a focal point at the sample area, so that light collected from the sample is collimated before passing through the filter 44, thereby ensuring maximum filter efficiency.

The microfluidic chip is fabricated with PDMS using conventional soft lithographic techniques. The mold for the chip is fabricated by adhering metallic sleeves onto a glass substrate using an epoxy, for example a medical epoxy, such as Loctite M-31 CL Hysol. The sleeves define the probe entrance channels and the fluidic channel. Once the chip is formed, the probes can be conveniently put in place by inserting them into the chip through the channels. By fixing the position of the channels, the relative alignment of excitation probe to the collection probe is ensured without any complex alignment. This technique has been successfully tested with channel sizes of 3 mm, but in principle, the approach could be used to make channels of the order of 100 µm.

Figure 5:
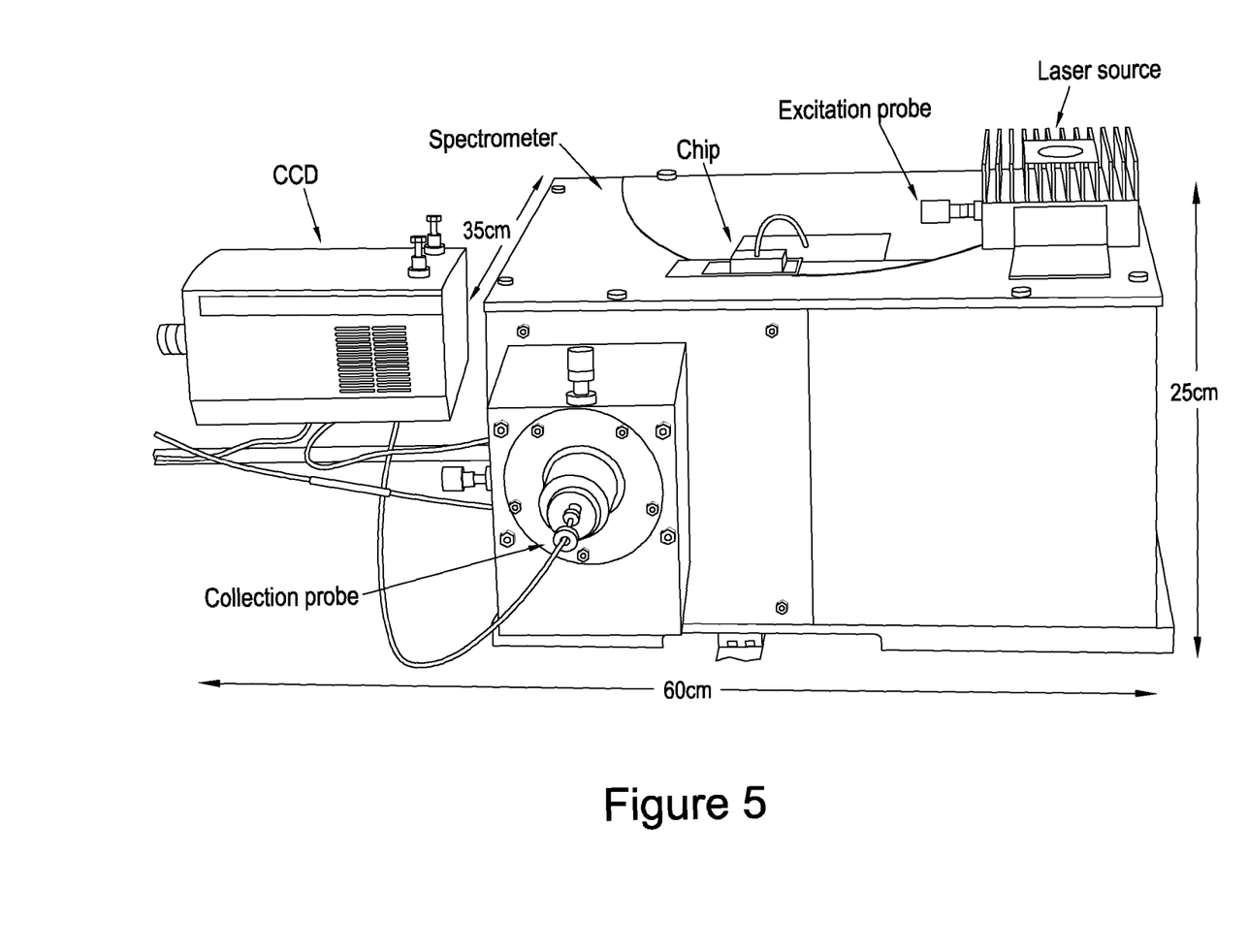
FIG. 5 is an image of a Raman spectroscopy system that includes the devices of FIG. 3.

FIG. 5 illustrates the microfluidic Raman chip included in a portable microfluidic Raman detection system. This has a diode laser, for example a 785 nm diode laser (Laser2000 (UK) Ltd.) with an output power of up to 200 mW for Raman excitation at the excitation probe head. The Raman excitation and the collection probes are coupled to the laser and the spectrometer (Shamrock SR-303i, Andor Technology) respectively using SMA connectors (Thorlabs Inc., USA). The spectrometer employs a 400 lines/mm grating, blazed at 850 nm and is equipped with a deep depletion, back-illuminated and thermoelectrically cooled CCD camera (Newton, Andor Technology) for the detection of Raman signal. The resolution of the Raman system is measured by the FWHM of the Silicon Raman peak at 520 cm$^{-1}$ and is found to be better than 6 cm$^{-1}$. The physical dimension of the whole system including the PDMS chip, Raman probe, laser source, spectrometer and CCD is 60 cm×35 cm×25 cm. The physical dimensions and the alignment free nature of the system make it portable. The probe based approach gives flexibility to the system such that it can reach otherwise inaccessible areas, a feature which has potential applications in online monitoring of the samples.

The throughput of an optical system is limited by the throughput of the most restrictive element. In a test device, a single multimode fiber was used for the collection probe. In practice, this fiber was the throughput restricting element. The numerical aperture (NA) of the collection fiber used in test was 0.22, and the core diameter was 200 µm. The throughput of the fiber was evaluated to be 0.0048 mm$^2$. The F number of the spectrometer was 4 and the slit height 8 mm. For a slit width of 200 µm, the throughput of this spectrometer would have been 0.0785 mm$^2$. However, since the collection fiber is coupled to the spectrometer, the throughput of the spectrometer is matched with that of the fiber using a pair of lenses which acts as an F-number matcher. Thus, the resulting throughput of the spectrometer was also 0.0048 mm$^2$sr. A 2.5 mm diameter filter was used with a 2.5 mm diameter achromatic doublet for collection, which has ~0.5NA. Therefore, the throughput of the collecting lens is higher compared to that of the collection fiber, which introduces a mismatch. However, the throughput of the whole system could be improved by using multiple fibers for collection.

The overlap volume of both excitation and collection probes can be used to estimate the overall collection volume for the device. The lenses at the tip of the probes are positioned in such a way that at orthogonal collection geometry, the focal points of the excitation and collection probes overlap. In the test device, the beam diameter at the focal spot was ~200 µm. Hence at orthogonal geometry, the collection volume could be approximated as a cube of edge 200 µm. The collection volume, from where the Raman spectrum of the sample is collected is estimated to be ~8 nanoliters.

Figure 6:
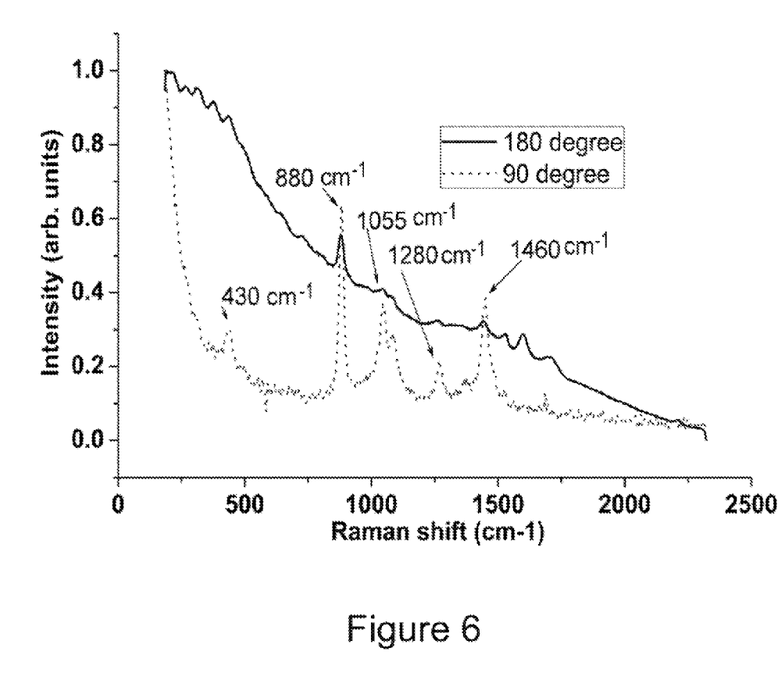
FIG. 6 shows two Raman signals, one measured using the device of FIGS. 3(a) and (b), and the other taken using the device of FIG. 3(c)

FIG. 6 shows a comparison of the Raman spectra of ethanol collected in the two geometries of FIGS. 3(a)/3(b) and FIG. 3(c). Each Raman spectrum is normalized with respect to its maximum intensity value. It can be seen from this that spectra recorded with the 90° (orthogonal) collection geometry have substantially lower background signal than the spectra collected with the 180° geometry. This background is primarily due to the fluorescence excited in the collection probe by forward scattering 785 nm light, which leaks through the imperfections in the periphery of the collection probe head.

To verify the source of enhanced background at 180° geometry, the Raman spectra was collected in the above specified geometries for de-ionized water and air (when there is no sample inside the chip). The background signal is high for 180° geometry, which confirms that the major contribution for the fluorescent background is from the fiber. The experiment with air showed no Raman peaks corresponding to PDMS, which ensures that the obtained Raman spectra does not have any cross talk signals from the material of the chip, unlike the other approaches where detection is performed externally.

The detection sensitivity of the system for measuring bioanalytes is demonstrated by detecting urea (Sigma Aldrich Inc.) close to physiological level of human urine. The concentration of urea in human fluids is an important indicator of proper kidney function in mammals. The sample solution of urea is gravimetrically prepared in deionized water for various concentrations ranging from 0.05M to 1M. The Raman spectra of the samples were acquired in the probe based microfluidic chip with an acquisition time of 5 s each.

The minimum detection limit of the system was determined by estimating the Noise Equivalent Concentration (NEC). NEC refers to the limiting value of concentration of the analyte of interest when signal level from the analyte of interest is just equal to the measurement noise, i.e. SNR=1. For the SNR calculation, the signal is calculated as the norm of mean of 10 measurements at a particular concentration, over the spectral bands where the signature of the analyte of interest appears. The noise is calculated as the norm of the standard deviation of the 10 measurements over the same spectral band. The well known characteristic peak of urea in the Raman fingerprint region at 999 $cm^{-1}$ was used. The SNR vs. concentration plot is given in FIG. 7. The value of NEC from was estimated to be 0.144M. Thus the results show that the minimum detection limit of our current system to detect urea is ~0.15M for an acquisition time of 5 s.

Figure 7:
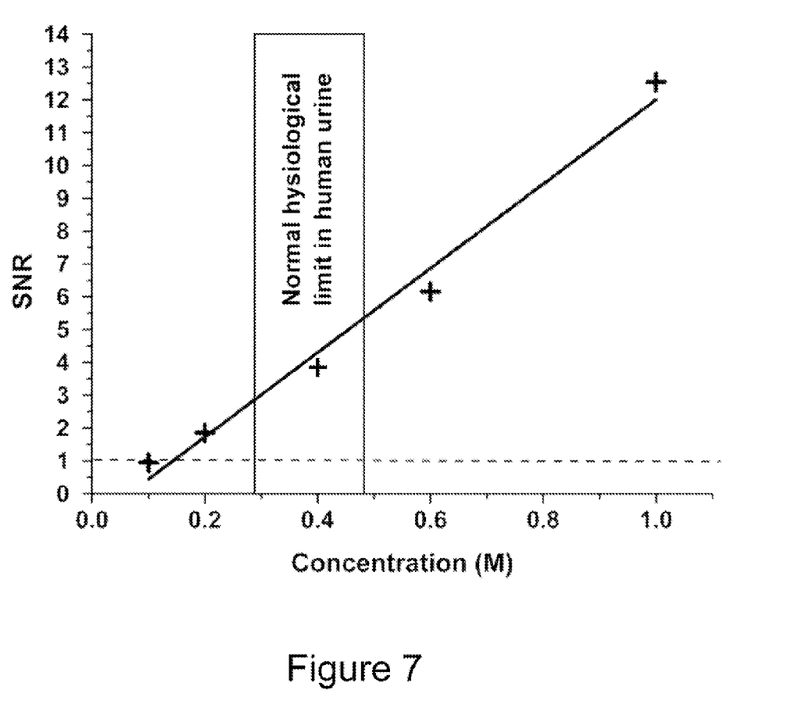
FIG. 7 is a plot of concentration vs. signal to noise ratio for a urea sample.

FIG. 7 shows that, with the estimated system performance characteristics, the system is capable of detecting concentration of urea at physiological level of human urine. The detection limit is two orders lower than state of the art bulk optics based Raman detection systems. However compared to the state of the art bulk optics systems, the system offers portability and alignment free detection of analyte. The detection limit of the present system can be further improved by improving the collection efficiency of the Raman probe and increasing the throughput of the system.

Figure 8:
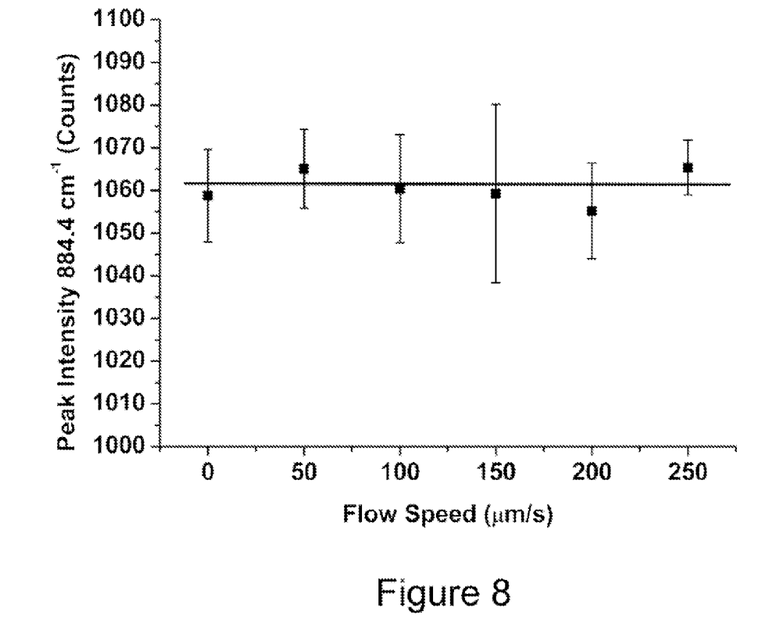
FIG. 8 is a plot of ethanol Raman peak intensity at 884 cm$^{-1}$ vs. flow speed.

To ensure the mechanical robustness of the device in flow based systems, the sensitivity under flow conditions was evaluated. Ethanol was flown through the microfluidic chip at different flow rates and Raman spectra were recorded for an acquisition time of 5 s each. The intensity, averaged over 10 spectra corresponding to one flow rate, of the strongest Raman peak at 884 $cm^{-1}$ is plotted against different flow rates as shown in FIG. 8. From FIG. 8, it is clear that the sensitivity of the system is not affected from the changing flow rates. This shows that the system is leak proof under pressure and there is no misalignment for the collection and excitation fiber due to the pressure introduced by the flow.

Because of the physical nature of the device, one chip can be used for detecting different samples, provided a proper rinsing procedure is carried out after flowing each chemical through the chip. The rinsing procedure can be done with any suitable cleaning fluid, for example de-ionized water. In order to verify the residual free nature of the chip, ethanol was flown through the chip, followed by de-ionized water for rinsing. Subsequently 0.4M urea was flown through the chip. The Raman spectra of urea were recorded with an acquisition time of 5 s. No peaks from ethanol were present in the recorded Raman spectra of urea proving that the rinsing procedure makes the chip 100% residual free and reusable.

The direct combination of a split Raman probe design and microfluidic platform enables the development of powerful, portable bio-chemical sensing devices. For some applications, the sensitivity is orders of magnitude better than conventional techniques. Because the system can be built on PDMS based microfluidic platform the technology is inexpensive and biocompatible.

The present invention provides a fiber probe based Raman detection system on a microfluidic platform where a split Raman probe is directly embedded into a microfluidic chip. In contrast to previous Raman detection schemes in microfluidics, the invention offers reduced background and portability. Compared to conventional backscattering probe designs, the split fiber probe used, results in a reduced size and offers flexibility to modify the collection geometry to minimize the background generated by the fibers. The invention provides an alignment free system with a low acquisition time. Development of this on a microfluidic platform means portable, robust, lab on a chip devices for biological analyte detection and environmental sensing using Raman spectroscopy are within reach.

A skilled person will appreciate that variations of the disclosed arrangements are possible without departing from the invention. For example although the excitation and collection probes of FIG. 3 are shown an orthogonal or collinear orientation, it will be appreciated that any relative angle could be used. For example, the probes could be arranged parallel to each other. In addition, multiple collection probes could be used simultaneously. Accordingly the above description of the specific embodiment is made by way of example only and not for the purposes of limitation. It will be clear to the skilled person that minor modifications may be made without significant changes to the operation described.

"The following paper is incorporated herein by reference: Ashok, P. C., Singh, G. P., Tan, K. M., and Dholakia, K. (Apr. 12, 2010), "Fiber probe based microfluidic raman spectroscopy," Optics Express, 18(8), 7642-7649."

The invention claimed is:

1. A microfluidic device for performing Raman spectroscopy comprising:
   at least one microfluidic channel with an input and an output for allowing fluid flow; and
   at least one Raman fiber based probe having an excitation fiber probe positioned so that one end of the excitation fiber probe is in the microfluidic channel and a collection fiber probe positioned so that one end of the collection fiber probe is in the microfluidic channel, the excitation fiber probe and the collection fiber probe are orthogonal to each other, wherein the excitation fiber probe includes an excitation probe head that is embedded in the microfluidic device and houses an end of the excitation fiber, a bandpass filter for blocking all light except excitation light, a collimator for collimating light incident on the bandpass filter, and lens for focusing excitation light onto a sample; and
   the collection fiber probe including a collection probe head that is embedded in the microfluidic device and houses an end of the collection fiber probe, a longpass filter for allowing Raman signals to pass the collection fiber probe and blocking excitation light, and a collimator for collimating light collected from the sample before it is incident on the longpass filter.

2. A device as claimed in claim 1 wherein the at least one Raman fiber based probe comprises at least one collection probe and at least one excitation probe located in a single housing.

3. A device as claimed in claim 1 wherein the excitation probe and the collection probe are located in separate probe housings.

4. A device as claimed in claim 3 wherein the at least one excitation probe and the at least one collection probe are positioned in a split probe configuration.

5. A device as claimed in claim 3 wherein the excitation probe and/or the collection probe are orthogonal to the microfluidic channel.

6. A device as claimed in claim 1 wherein the at least one Raman probe is embedded within material forming the microfluidic channel.

7. A device as claimed in claim 1 wherein the at least one Raman probe is located or embedded in one or more channels within material forming the microfluidic channel.

8. A device as claimed in claim 1 wherein the collimator for collimating the light incident on the bandpass filter comprises a pair of achromatic doublets.

9. A device as claimed in claim 1 wherein the collimator for collimating the light collected from the sample comprises a pair of achromatic doublets.

10. A device as claimed in claim 1 wherein a material forming the microfluidic channel is molded.

11. A Raman spectroscopy system that comprises:
a microfluidic device comprising at least one microfluidic channel with an input and an output for allowing fluid flow;
at least one Raman fiber based probe having an excitation fiber probe positioned so that one end of the excitation fiber probe is in the microfluidic channel and a collection fiber probe positioned so that one end of the collection probe is in the microfluidic channel, wherein the excitation fiber probe and the collection probe are orthogonal to each other, wherein the excitation fiber probe includes an excitation probe head that is embedded in the microfluidic device and houses an end of the excitation fiber, a bandpass filter for blocking all light except excitation light, a collimator for collimating light incident on the bandpass filter, and lens for focusing excitation light onto a sample and the collection fiber probe including a collection probe head that is embedded in the microfluidic device and houses an end of the collection fiber probe, a longpass filter for allowing Raman signals to pass the collection fiber probe and blocking excitation light, and a collimator for collimating light collected from the sample before it is incident on the longpass filter;
a laser for use as an excitation source; and
a spectroscope for analyzing Raman signals collected by the collection probe.

* * * * *

UNITED STATES PATENT AND TRADEMARK OFFICE
CERTIFICATE OF CORRECTION

PATENT NO. : 8,638,431 B2  
APPLICATION NO. : 12/892640  
DATED : January 28, 2014  
INVENTOR(S) : Praveen Cheriyan Ashok et al.

Page 1 of 1

It is certified that error appears in the above-identified patent and that said Letters Patent is hereby corrected as shown below:

On the Title Page, Item (54) and in the Specification, Column 1, Lines 1-2, Title should read: "FIBER PROBE BASED MICROFLUIDIC RAMAN SPECTROSCOPY"

Signed and Sealed this
Tenth Day of June, 2014

Michelle K. Lee
*Deputy Director of the United States Patent and Trademark Office*